United States Patent [19]

Magnani

[11] 3,966,942
[45] June 29, 1976

[54] 3-SUBSTITUTED-5-HYDROXY(MERCAPTO)ALKYLIDENE-RHODANINE DERIVATIVES

[75] Inventor: Arthur Magnani, Wynnewood, Pa.

[73] Assignee: SmithKline Corporation, Philadelphia, Pa.

[22] Filed: Mar. 14, 1975

[21] Appl. No.: 558,399

Related U.S. Application Data

[60] Division of Ser. No. 379,037, July 13, 1973, Pat. No. 3,890,331, which is a continuation-in-part of Ser. No. 254,363, May 18, 1972, abandoned.

[30] Foreign Application Priority Data

May 3, 1973    United Kingdom............... 21064/73

[52] U.S. Cl................................. 424/263; 424/270
[51] Int. Cl.² ................ A61K 31/44; A61K 31/425
[58] Field of Search............................ 424/263, 270

[56] References Cited

UNITED STATES PATENTS

| | | | |
|---|---|---|---|
| 2,658,890 | 11/1953 | Croxall | 260/240 |
| 2,713,579 | 7/1955 | Knott | 260/240.1 |
| 2,739,970 | 3/1956 | Knott | 260/306.7 |
| 2,839,404 | 6/1958 | Knott | 96/105 |

OTHER PUBLICATIONS

Behringer et al., Berichte, 91, 2773–2783 (1958).
Lo et al., J. Amer. Chem. Soc., 76, 4166–4169 (1954).
Knott, J. Chem. Soc. (1954), 1482–1490.

*Primary Examiner*—Norman A. Drezin
*Attorney, Agent, or Firm*—Richard D. Foggio; Wm. H. Edgerton

[57] ABSTRACT

3-Substituted-5-hydroxy(mercapto)alkylidene-rhodanine derivatives in which the 3-substituent is lower alkyl, cycloalkyl, alkenyl, phenyl, phenylalkyl, substituted phenyl or pyridylmethyl and having antiarthritic activity are generally prepared from the appropriate 5-unsubstituted rhodanine by reaction with an orthoester followed by alkaline hydrolysis of the intermediate 5-alkoxyalkylidene rhodanine to give the 5-hydroxyalkylidene products or treatment of the intermediate rhodanine derivative with sodium sulfide to give the 5-mercaptoalkylidene products.

9 Claims, No Drawings

3-SUBSTITUTED-5-HYDROXY(MERCAPTO)ALKYLIDENE-RHODANINE DERIVATIVES

This is a division of application Ser. No. 379,037, filed July 13, 1973, now U.S. Pat. No. 3,890,331 which is a continuation-in-part of Ser. No. 254,363 filed May 18, 1972, now abandoned.

This invention relates to novel 3-substituted-5-hydroxy(mercapto)alkylidene-rhodanine derivatives having useful pharmacodynamic activity. More specifically the compounds of this invention have anti-arthritic activity as measured by their ability to inhibit or suppress adjuvant-induced polyarthritis in rats. Thus the compounds of this invention decrease the inflamed hind leg volumes in experimental rats when compared to controls at oral doses of from 12.5 to 100 mg/kg/day.

The compounds of this invention are represented by the following structural formula:

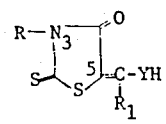

FORMULA I wherein:

R represents lower alkyl of from 1 to 4 carbon atoms, straight or branched chain, cycloalkyl of from 3 to 6 carbon atoms for example cyclopropyl or cyclohexyl, alkenyl of from 3 to 5 carbon atoms for example allyl or dimethylallyl, phenyl, phenylalkyl of from 7 to 9 carbon atoms, substituted phenyl, such as monohalophenyl for example monochloro, monobromo or monofluorophenyl, dichlorophenyl for example 2,6-dichlorophenyl or 3,4-dichlorophenyl, alkylphenyl for example tolyl, or methylchlorophenyl for example 2-chloro-4-methylphenyl, or pyridylmethyl for example 2-, 3-or 4-pyridylmethyl;

$R_1$ represents lower alkyl of from 1 to 4 carbon atoms, phenylalkyl of from 7 to 9 carbon atoms, said alkyl moieties may be straight or branched chain, or substituted benzyl, such as monochloro or monomethylbenzyl, and Y represents oxygen or sulfur.

Preferred compounds of formula I are those wherein R is methyl, ethyl, propyl butyl, phenyl, monochlorophenyl, especially when the latter is 2'-or 4'-chlorophenyl, cyclohexyl or benzyl, $R_1$ is methyl, ethyl, benzyl or phenethyl, and Y is oxygen.

The compounds of formula I above wherein Y is oxygen are prepared by reaction of the appropriate 5-unsubstituted rhodanine with an orthoester in acetic anhydride followed by alkaline hydrolysis of the intermediate 5-alkoxyalkylidene rhodanine shown as follows:

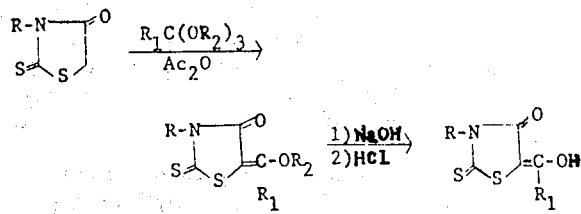

in which R and $R_1$ are as defined above and $R_2$ is methyl or ethyl. The initial reaction is advantageously carried out at reflux temperature for from four to twenty hours. The separated intermediate in a solvent such as aqueous dioxane or aqueous methanol is hydrolyzed with dilute aqueous sodium hydroxide solution preferably at room temperature for several hours. Acidification of the reaction mixture with dilute hydrochloric acid gives the 5-hydroxyalkylidene rhodanine derivative.

Alternatively, good yields of the intermediate 5-alkoxyalkylidene rhodanine intermediates are obtained by heating the 5-unsubstituted rhodanine with the orthoester at a temperature of about 150°C. for from ½ to 3 hours.

The compounds of formula I wherein Y is sulfur are prepared from the intermediate 5-alkoxyalkylidene rhodanines, obtained as outlined above, by reaction with sodium sulfide in aqueous ethanol at room temperature for from 15 to 60 minutes followed by acidification of the reaction product with hydrochloric acid.

The 5-unsubstituted rhodanines used as starting materials described hereinabove are either known or are prepared by one of the following synthetic methods. Starting with an isothiocyanate, a compound of the formula R-N=C=S is condensed with an excess of mercaptoacetic acid in the presence of triethylamine, by heating in a pressure bottle at 100°–140°C. for from one to four hours to give the desired 3-R-substituted rhodanine. The required isothiocyanates are prepared, for example, by the reaction of an appropriate amine ($RNH_2$) with thiophosgene ($CSCl_2$). Starting with a dithiocarbamate, a compound of the formula

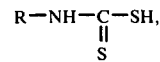

preferably as a triethylamine salt, is condensed with chloroacetic acid (or ester) followed by treatment with mineral acid to give the rhodanine derivative.

The required orthoester reactants are prepared by known procedures from the appropriate cyanide shown, for example, as follows:

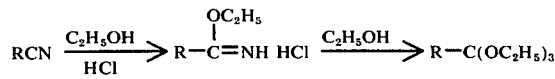

in which R is as defined in formula I.

Several 5-hydroxymethylene rhodanines have been described in the literature. Ber. 91, 2773 (1958), as well as 5-methoxymethylene, 5-ethoxymethylene, 5-ethoxyethylidene and 5-ethoxypropylidene rhodanines, J.A.C.A. 76, 4166 (1954) and J. Chem. Soc. 1954 1482. However no biological use has been described for these rhodanine derivatives and none have been found to have significant anti-arthritic activity.

The compounds of this invention are administered in conventional dosage unit forms by incorporating an amount sufficient to produce anti-arthritic activity with a nontoxic pharmaceutical carrier according to accepted procedures. Preferably the dosage units will contain a compound of formula I in an amount of from about 10 mg. to about 200 mg. per unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent includes any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The method of producing anti-arthritic activity in accordance with this invention comprises administering internally to an animal organism a compound of formula I above, usually combined with a pharmaceutical carrier, in an amount sufficient to produce anti-arthritic activity without limiting side effects. The active medicament will be administered in a dosage unit, as described above, orally or parenterally, the oral route being preferred. Advantageously equal doses will be administered one or two times daily with the daily dosage regimen being from about 10 mg. to about 400 mg. When the method described above is carried out, anti-arthritic activity is produced with a minimum of side effects.

The pharmaceutical preparations are made following the conventional techniques of the pharmaceutical chemist involving mixing, granulating and compressing when necessary, or variously mixing and dissolving the ingredients as appropriate to the desired end product.

The following examples illustrate the preparation of compounds of this invention and their incorporation into pharmaceutical compositions, and as such are not to be considered as limiting the invention set forth in the claims appended hereto.

EXAMPLE 1

A mixture of 27 g. (0.16 m.) of p-chlorophenyl isothiocyanate, 33 ml. (42.5 g., 0.475 m.) of mercaptoacetic acid and 5 drops of triethylamine is heated in a pressure bottle at 120°–130°C. for 2½ hours. The reaction mixture is allowed to stand at room temperature overnight and filtered. The crude product is recrystalized from ethanol to give 3-(4'-chlorophenyl)-rhodanine, m.p. 124.5°–126°C.

A mixture of 50 g. (0.2 m.) of the above-prepared rhodanine and 140 g. (0.86 m.) of triethylorthoacetate in 350 ml. of acetic anhydride is refluxed for four hours. The cooled reaction solution is filtered and the product is washed with 100 ml. of 70% aqueous acetic acid to yield 3-(4'-chlorophenyl)-5-(1'-ethoxyethylidene)-rhodanine, m.p. 168°–171°C.

To a mixture of 32 g. (0.1 m.) of 3-(4'-chlorophenyl)-5-(1'-ethoxyethylidene)-rhodanine in 400 ml. of water and 250 ml. of methanol is added 85 ml. of 5% sodium hydroxide solution and the resulting suspension is stirred at room temperature for 5 hours. The reaction mixture is filtered and the filtrate is decolorized, then acidified with dilute hydrochloric acid to give 3-(4'-chlorophenyl)-5-(1'-hydroxyethylidene)-rhodanine, m.p. 200°–205°C.

EXAMPLE 2

Following the procedures of Example 1, triethylorthopropionate is reacted with 3-(4'-chlorophenyl)-rhodanine in acetic anhydride for 5½ hours to give 3-(4'-chlorophenyl)-5-(1'-ethoxypropylidene)-rhodanine. To a suspension of the latter (25 g., 0.0765 m.) in 200 ml. of dioxane and 200 ml. of water is added 50 ml. of 10% sodium hydroxide solution. The mixture is stirred at room temperature for 4 hours and then concentrated in vacuo at 40°–45°C. The residual solution is washed with ether, decolorized and acidified with dilute hydrochloric acid to yield 3-(4'-chlorophenyl)-5-(1'-hydroxypropylidene)-rhodanine, m.p. 145°–149°C.

EXAMPLE 3

As described in Example 1, triethylorthophenylacetate is reacted with 3-(4'-chlorophenyl)-rhodanine in acetic anhydride for 12 hours to yield 3-(4'-chlorophenyl)-5-(1'-ethoxy-2'-phenylethylidene)-rhodanine. To a suspension of the latter (15 g., 0.0385 m.) in 100 ml. of dioxane and 100 ml. of water is added 22 ml. of 10% sodium hydroxide solution. The mixture is stirred at room temperature for 3 hours, concentrated in vacuo at 40°–40°C. and the remaining solution is washed with ether, then decolorized. The aqueous layer is acidified with dilute hydrochloric acid and the precipitate is taken up in methylene chloride. The latter solution (after being washed with water and dried) is evaporated in vacuo. The residue is dissolved in 10% sodium hydroxide and water, washed with ether and acidified with dilute hydrochloric acid to give 3-(4'-chlorophenyl)-5-(1'-hydroxy-2'-phenylethylidene)-rhodanine, m.p. 134°–137°C.

EXAMPLE 4

To a suspension of 3 g. (0.091 m.) of 3-(4'-chlorophenyl)-5-(1'-ethoxypropylidene)-rhodanine in 15 ml. of ethanol is added a solution of sodium sulfide in 10 ml. of water and the mixture is stirred at room temperature until solution is complete (15–20 minutes). This solution is added to 100 ml. of water, allowed to stand for 15 minutes, filtered and the filtrate is acidified with 2N hydrochloric acid to give 3-(4'-chlorophenyl)-5-(1'-mercaptopropylidene)-rhodanine, m.p. 163°–165°C.

EXAMPLE 5

A mixture of 25 g. (0.12 m.) of 3-phenylrhodanine, 80 g. (0.34 m.) of triethylorthophenylacetate [prepared as described in J.A.C.S. 68, 1917 (1946)] and 250 ml. of acetic anhydride is heated under reflux for 20 hours and the solution is then concentrated in vacuo. The residue is filtered and the solid is stirred with 160 ml. of dioxane, 160 ml. of water and 40 ml. of 10% sodium hydroxide for 4 hours. The solution is concentrated in vacuo at 35°–40°C. to evaporate the dioxane. The aqueous solution, after washing with ether and decolorizing with charcoal, is made acidic with dilute hydrochloric acid. The solid product is purified by chromatography to give 5-(1'-hydroxy-2'-phenylethylidene)-3-phenyl-rhodanine, m.p. 146–148°C.

Alternatively, a mixture of 6 g. (0.029 m.) of 3-phenyl-rhodanine, 15 g. (0.063 m.) of triethylorthophenylacetate and 15 ml. of n-butyl ether is heated to reflux and then distillate is removed until the temperature of the mixture reaches 150°C. After heating at this temperature for one hour, an additional 5 g. of orthoester is added and heating is continued for 30 minutes. To the reaction mixture is added 5 ml. of acetic anhydride and heating is continued for 5 minutes. The resulting mixture is concentrated in vacuo and the residue is eluted through a column of silica gel with 2:1-cyclohexane-benzene. The product from the first eluates give 5-(1'-ethoxy-2'-phenylethylidene)-3-phenylrhodanine, m.p. 119°–121°C. Alkaline hydrolysis as described above of this intermediate furnishes the identical hydroxy derivative.

EXAMPLE 6

A mixture of 7.5 g. (0.05 m.) of 3-ethylrhodanine, 25 g. (0.128 m.) of trimethylorthophenylacetate and 80 ml. of acetic anhydride is heated under reflux for 18 hours. The solution is concentrated in vacuo and the residue chromatographed through silica gel using 50% benzene in cyclohexane as the eluant to give 3-ethyl-5-(1'-methoxy-2'-phenylethylidene)-rhodanine, m.p. 120°–122°C.

The above prepared 5-substituted rhodanine (2 g., 0.0068 m.) is stirred with 25 ml. of dioxane, 20 ml. of water and 8 ml. of 10% sodium hydroxide solution for 2½ hours. The resulting solution is concentrated in vacuo at 40°C. to remove dioxane. The aqueous solution is washed with ether and acidified with dilute hydrochloric acid to yield 3-ethyl-5-(1'-hydroxy-2'-phenylethylidene)-rhodanine, m.p. 74°–76°C.

EXAMPLE 7

A mixture of 5 g. (0.033 m.) of 3-ethylrhodanine, 12 ml. of triethylorthoacetate and 35 ml. of acetic anhydride is heated under reflux for 18 hours and the solution is then concentrated in vacuo. The cooled residue is filtered and the solid is dissolved in ether. The ether solution is washed with water, dried and evaporated in vacuo to give 5-(1'-ethoxyethylidene)-3-ethylrhodanine. The latter (3.6 g.) is stirred with 15 ml. of dioxane, 15 ml. of water and 15 ml. of 10% sodium hydroxide solution for 4 hours. The resulting solution is concentrated in vacuo at 40°C. and the aqueous solution is washed with ether, decolorized, then made acidic with dilute hydrochloric acid. The precipitate is dissolved in 10% sodium hydroxide solution, washed with ether and the aqueous solution is made acidic with dilute hydrochloric acid to give the product, 3-ethyl-5-(1'-hydroxyethylidene)-rhodanine, m.p. 93°C.

EXAMPLE 8

A mixture of 8.4 g. (0.04 m.) of 3-phenylrhodanine, 21 g. (0.12 m.) of triethylorthopropionate and 80 ml. of acetic anhydride is heated under reflux for six hours, cooled and filtered. The solid is washed with 50% aqueous acetic acid to afford 5-(1'-ethoxypropylidene)-3-phenylrhodanine, m.p. 178°–181°C.

The above prepared ethoxy derivative (10 g. 0.034 m.) in 80 ml. of dioxane, 80 ml. of water and 20 ml. of 10% sodium hydroxide solution is stirred for 4 hours. The resulting solution is concentrated in vacuo at 35°–40°C. and the aqueous solution is washed with ether, followed by acidification with dilute hydrochloric acid to yield 5-(1'-hydroxypropylidene)-3-phenylrhodanine, m.p. 105°–111°C.

EXAMPLE 9

A mixture of 24.4 g. (0.1 m.) of 3-(4'-chlorophenyl)-rhodanine, 80 g. of trimethyl β-phenylorthopropionate [prepared as described in J.A.C.S. 69, 2665 (1947)] and 150 ml. of acetic anhydride is heated under reflux for 18 hours. Upon standing at room temperature the solid separates from the reaction mixture which is filtered and washed with acetic acid to give 3-(4'-chlorophenyl)-5-(1'-ethoxy-3'-phenylpropylidene)-rhodanine. The latter (20 g. 0.052 m.) is stirred at room temperature with 250 ml. of dioxane, 250 ml. of water and 35 ml. of 10% sodium hydroxide solution for 2 hours. The solution is concentrated in vacuo at 40°C. and then washed with ether. The aqueous solution is made acidic with dilute hydrochloric acid to give 3-(4'-chlorophenyl)-5-(1'-hydroxy-3'-phenylpropylidene)-rhodanine, m.p. 170°14 173°C.

EXAMPLE 10

As described in Example 1, a mixture of 6.12 g. (0.04 m.) of p-fluorophenyl isothiocyanate, 4.15 ml. (5.5 g., 0.06 m.) of mercaptoacetic acid and 5 drops of triethylamine is heated in a pressure bottle at 110°–130°C. for 3 hours to yield after cooling and filtration the product, 3-(4'-fluorophenyl)-rhodanine, m.p. 155°–158°C.

Similar reaction of this rhodanine (0.2 m.) with 140 g. (0.86 m.) of triethylorthoacetate in 350 ml. of acetic anhydride followed by alkaline hydrolysis of the intermediate 5-(1'-ethoxyethylidene)-3-(4'-fluorophenyl)-rhodanine gives the corresponding 3-(4'-fluorophenyl)-5-(1'-hydroxyethylidene)-rhodanine.

EXAMPLE 11

To a solution of 4.73 g. (0.05 m.) of chloroacetic acid in 40 ml. of water is added a solution of 2.7 g. (0.025 m.) of sodium carbonate in 20 ml. of water. The solution is cooled in an ice bath and 14.2 g. (0.05 m.) of the triethylamine salt of p-tolyl dithiocarbamic acid is added portionwise over five minutes. The resulting mixture is stirred at room temperature for 1½ hours. Water is added to bring total volume to 150 ml. and the resulting mixture is warmed on the steam bath for 5 minutes, then filtered. The filtrate is acidified with 40 ml. of 6N hydrochloric acid, heated to 95°C., cooled, filtered and the solid washed with water to leave 3-(4'-tolyl)-rhodanine, m.p. 164°–165°C.

Following the procedures of Examples 1 and 2, triethylorthopropionate is reacted with 3-(4'-tolyl)-rhodanine in acetic anhydride to give 5-(1'-ethoxypropylidene)-3-(4'-tolyl)-rhodanine. The latter is hydrolyzed with 10% sodium hydroxide solution to yield upon workup, 5-(1'-hydroxypropylidene)-3-(4'-tolyl)-rhodanine.

EXAMPLE 12

A mixture of 6.12 g. (0.03 m.) of 3,4-dichlorophenyl isothiocyanate, 2.8 ml. (3.68 g., 0.04 m.) of mercaptoacetic acid and a few drops of triethylamine is heated in a pressure bottle at 110°–130°C. for 2 hours. The cooled reaction mixture is filtered to give 3-(3',4'-dichlorophenyl)-rhodanine, m.p. 176°–178°C.

The rhodanine is reacted as described in Examples 1 and 3 with triethylorthophenylacetate in acetic anhydride to yield 3-(3',4'-dichlorophenyl)-5-(1'-ethoxy-2'-phenylethylidene)-rhodanine which is similarly hydrolyzed to 3-(3',4'-dichlorophenyl)-5-(1'-hydroxy-2'-phenylethylidene)-rhodanine.

Similarly, employing 2-chloro-4-methylphenyl isothiocyanate as described above yields the corresponding 3-(2'-chloro-4'-methylphenyl)-rhodanine which is reacted with triethylorthophenylacetate and the intermediate 5-alkoxy derivative is hydrolyzed to give 3-(2'-chloro-4'-methylphenyl)-5-(1'-hydroxy-2'-phenylethylidene)-rhodanine.

EXAMPLE 13

| Ingredients | Mg./Tablet |
|---|---|
| 3-(4'-chlorophenyl)-5-(1'-hydroxy-3'-phenylpropylidene)-rhodanine | 25 |
| Calcium sulfate, dihydrate | 150 |
| Sucrose | 25 |
| Starch | 15 |
| Talc | 5 |
| Stearic acid | 3 |

The sucrose, calcium sulfate and 3-(4'-chlorophenyl)-5-(1'-hydroxy-3'-phenylpropylidene)-rhodanine are thoroughly mixed and granulated with hot 10% gelatin solution. The wetted mass is passed through a No. 6 mesh screen directly onto drying trays. The granules are dried at 120°F. and passed through a No. 20 mesh screen, mixed with the starch, talc and stearic acid, and compressed into tablets.

EXAMPLE 14

| Ingredients | Mg./Capsule |
|---|---|
| 3-(4'-chlorophenyl)-5-(1'-hydroxy-3'-phenylpropylidene)-rhodanine | 150 |
| Magnesium stearate | 5 |
| Lactose | 300 |

The above ingredients are screened through a No. 40 mesh screen, mixed and filled with No. 0 hard gelatin capsules.

Similarly, by employing the methods described herein the following 5-(1'-hydroxyalkylidene)-rhodanine derivatives were prepared from corresponding 5-(1'-ethoxyalkylidene)-rhodanine intermediates. The intermediates were prepared by one of the following methods:

A. The 3-substituted rhodanine is refluxed with the appropriate orthoester in acetic anhydride for a period of from 16–18 hours using 1 mole of rhodanine, 3 moles of orthoester and approximately 5 moles of acetic anhydride. The reaction mixture is worked up by concentration in vacuo to remove the acetic anhydride, then crystallization by the addition of petroleum ether. Alternatively the residue is chromatographed on a silica gel column, eluting with mixtures of cyclohexane-benzene.

B. The 3-substituted rhodanine is heated with the appropriate orthoester (2–3 moles) at a temperature of 150°–155°C. for a period of from 2–3 hours, with workup as in (A).

The final products are obtained by hydrolyzing the intermediates in 3 to 5 parts by volume of dioxane to which is added 3 parts by volume of 10% sodium hydroxide solution followed by 3 parts by volume of water. The mixture is stirred at room temperature for 1–2 hours to affect complete hydrolysis, then concentrated in vacuo to remove most of the dioxane. The residual solution is extracted with ether and the product is precipitated by acidification with dilute hydrochloric acid.

TABLE I

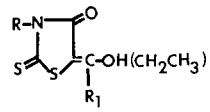

| Example | R | R₁ | Ethoxy Intermediate Method | M.P. °C. | Hydroxy Product M.P. °C. |
|---|---|---|---|---|---|
| 15 | 4-chlorophenyl | 4-chlorobenzyl | B | 118–120 | 133–135 |
| 16 | 4-chlorophenyl | 4-methylbenzyl | B | 165–166 | 139–140 |
| 17 | isopropyl | benzyl | B | 105–106 | 91–93 |
| 18 | 4-chlorophenyl | isobutyl | B | 106–107 | 168–170 |
| 19 | n-propyl | benzyl | B | 66–68 | 68–69 |
| 20 | isobutyl | benzyl | B | syrup | 91–93 |
| 21 | benzyl | benzyl | B | 111–116 | 108–110 |
| 22 | ethyl | ethyl | B | 62–64 | 45–46 |
| 23 | isopropyl | ethyl | A | 55–57 | 55–56 |
| 24 | benzyl | ethyl | A | 98–99 | 93 |
| 25 | allyl | ethyl | A | 60–61 | 72–74 |
| 26 | isobutyl | ethyl | A | 59–61 | 78–79 |
| 27 | cyclopropyl | ethyl | B | 75–78 | 103 |
| 28 | n-butyl | ethyl | A | 39–41 | 50–52 |
| 29 | cyclohexyl | ethyl | A | 91–93 | 100–101 |
| 30 | phenethyl | ethyl | B | 97–98 | 118–119 |
| 31 | sec-butyl | ethyl | B | syrup | syrup |
| 32 | n-propyl | ethyl | B | 52–54 | 68–69 |
| 33 | methyl | ethyl | B | 96–98 | 95–98 |
| 34 | 3-pyridylmethyl | ethyl | A | 86–88 | 186 |
| 35 | 2-pyridylmethyl | ethyl | A | 82–83 | 215–216 |
| 36 | crotyl | ethyl | A | 48–50 | 68–71 |
| 37 | 2'-methylallyl | ethyl | A | 46–48 | 53–55 |

Also useful are amine salts of the compounds of formula I, for example, salts formed with 2-aminopyridine and 2-aminothiazole. Such salts similarly have antiarthritic activity and are prepared as follows:

a. A solution containing 3.6 g. of 3-ethyl-5-(1'-hydroxy-2'-phenylethylidene)-rhodanine (prepared as in Example 6) and 1.2 g. of 2-aminopyridine in 25 ml. of 30% aqueous methanol is warmed on a steam bath for 5 minutes. The resultant reddish solution is then concentrated to remove most of the methanol and allowed to crystallize. The crude product is isolated by filtration and recrystallized by dissolving in aqueous methanol, decolorizing and concentrating the solution to afford 3.8 g. of the amine salt, m.p. 133°–135°C.

b. In the same manner 2.8 g. of 3-ethyl-5-(1'-hydroxy-2'-phenylethylidene)-rhodanine is warmed in 25 ml. of 50% aqueous methanol with 1 g. of 2-aminothiazole. The reddish solution is decolorized, concentrated and allowed to crystallize to give 2.85 g. of the amine salt as yellow crystals, m.p. 110°–112°C.

What is claimed is:

1. A pharmaceutical composition having anti-arthritic activity, in dosage unit form, comprising a pharmaceutical carrier and an effective, nontoxic amount of a compound of the formula:

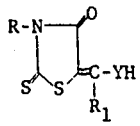

wherein:
R is lower alkyl of from 1 to 4 carbon atoms, straight or branched chain, cycloalkyl of from 3 to 6 carbon atoms, alkenyl of from 3 to 5 carbon atoms, phenyl, phenylalkyl of from 7 to 9 carbon atoms, monohalophenyl, dichlorophenyl, tolyl, methylchlorophenyl or pyridylmethyl;
$R_1$ is lower alkyl of from 1 to 4 carbon atoms, phenylalkyl of from 7 to 9 carbon atoms, said alkyl moieties being straight or branched chain, monochlorobenzyl or monomethylbenzyl; and
Y is oxygen or sulfur, or a 2-aminopyridine or 2-aminothiazole salt thereof.

2. The composition of claim 1 in which Y is oxygen.

3. The composition of claim 2 in which R is lower alkyl, phenyl, monochlorophenyl, cyclohexyl or benzyl.

4. The composition of claim 3 in which $R_1$ is methyl, ethyl, benzyl or phenethyl.

5. The composition of claim 4 in which R is cyclohexyl and $R_1$ is ethyl.

6. The composition of claim 1 in which the active medicament is in an amount of about 10 mg. to about 200 mg. per dosage unit.

7. The method of producing anti-arthritic activity which comprises administering internally to an animal in an amount sufficient to produce said activity a compound of the formula:

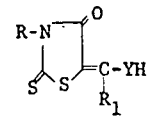

wherein:
R is lower alkyl of from 1 to 4 carbon atoms, straight or branched chain, cycloalkyl of from 3 to 6 carbon atoms, alkenyl of from 3 to 5 carbon atoms, phenyl, phenylalkyl of from 7 to 9 carbon atoms, monohalophenyl, dichlorophenyl, tolyl, methylchlorophenyl or pyridylmethyl;
$R_1$ is lower alkyl of from 1 to 4 carbon atoms, phenylalkyl of from 7 to 9 carbon atoms, said alkyl moieties being straight or branched chain, monochlorobenzyl or monomethylbenzyl; and
Y is oxygen or sulfur, or a 2-aminopyridine or 2-aminothiazole salt thereof.

8. The method of claim 7 in which R is cyclohexyl, $R_1$ is ethyl and Y is oxygen.

9. The method of claim 7 in which the active medicament is administered in a daily dosage regimen of about 10 mg. to about 400 mg.

* * * * *